United States Patent
Harris, Jr.

(10) Patent No.: US 8,369,891 B2
(45) Date of Patent: *Feb. 5, 2013

(54) WIRELESS TELEPHONY DEVICE WITH BREATH ANALYSIS SENSOR AND METHODS FOR USE THEREWITH

(76) Inventor: Patrick G. Harris, Jr., Cedar Park, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/572,791

(22) Filed: Aug. 13, 2012

(65) Prior Publication Data

US 2012/0329490 A1   Dec. 27, 2012

Related U.S. Application Data

(63) Continuation of application No. 12/403,513, filed on Mar. 13, 2009, now Pat. No. 8,280,436.

(51) Int. Cl.
| | |
|---|---|
| H04M 1/00 | (2006.01) |
| H04W 24/00 | (2009.01) |
| B60K 28/00 | (2006.01) |
| G08B 23/00 | (2006.01) |
| G01M 17/00 | (2006.01) |
| G01C 21/00 | (2006.01) |

(52) U.S. Cl. .......... 455/556.1; 455/456.1; 180/272; 340/576; 701/29; 701/207

(58) Field of Classification Search .......... 455/566
See application file for complete search history.

(56) References Cited

U.S. PATENT DOCUMENTS

| | | | | |
|---|---|---|---|---|
| 6,336,354 B1 * | 1/2002 | Suzuki et al. | ........... | 73/31.05 |
| 6,697,732 B1 * | 2/2004 | Gotfried | ........... | 701/516 |
| 6,853,956 B2 * | 2/2005 | Ballard et al. | ........... | 702/183 |
| 6,899,684 B2 * | 5/2005 | Mault et al. | ........... | 600/531 |
| 7,158,912 B2 * | 1/2007 | Vock et al. | ........... | 702/142 |
| 7,301,464 B2 * | 11/2007 | Coulter | ........... | 340/573.7 |
| 7,658,255 B2 * | 2/2010 | Nordin | ........... | 180/272 |
| 7,841,224 B2 * | 11/2010 | Son | ........... | 73/1.02 |
| 7,904,219 B1 * | 3/2011 | Lowrey et al. | ........... | 701/32.3 |
| 7,934,577 B2 * | 5/2011 | Walter et al. | ........... | 180/272 |
| 2002/0084130 A1 * | 7/2002 | Der Ghazarian et al. | ........... | 180/272 |
| 2002/0154035 A1 * | 10/2002 | Flick | ........... | 340/988 |
| 2003/0033032 A1 * | 2/2003 | Lind et al. | ........... | 700/52 |
| 2006/0182661 A1 * | 8/2006 | Aquila | ........... | 422/84 |
| 2006/0193749 A1 * | 8/2006 | Ghazarian et al. | ........... | 422/83 |
| 2006/0202842 A1 * | 9/2006 | Sofer | ........... | 340/576 |
| 2006/0244461 A1 * | 11/2006 | Song et al. | ........... | 324/500 |
| 2007/0193335 A1 * | 8/2007 | Son | ........... | 73/23.3 |
| 2008/0227466 A1 * | 9/2008 | Rabanne et al. | ........... | 455/456.1 |
| 2009/0164141 A1 * | 6/2009 | Lee | ........... | 702/30 |
| 2009/0325639 A1 * | 12/2009 | Koehn | ........... | 455/556.1 |
| 2010/0234064 A1 * | 9/2010 | Harris, Jr. | ........... | 455/556.1 |
| 2011/0088446 A1 * | 4/2011 | Son | ........... | 73/1.06 |
| 2011/0121965 A1 * | 5/2011 | Betts et al. | ........... | 340/539.13 |

\* cited by examiner

*Primary Examiner* — Dwayne Bost
*Assistant Examiner* — Scott Trandai
(74) *Attorney, Agent, or Firm* — Garlick & Markison; Bruce E. Stuckman

(57) ABSTRACT

A wireless telephony device includes a memory that stores at least one telephony application. A processor executes the telephony application to process at least one telephone call via a wireless telephony network in response to commands of a user. A breath analyzing sensor analyzes a breath of the user in conjunction with the at least one telephone call and generates breath analysis test data in response thereto. The telephony application generates a breath analysis test message, based on the breath analysis test data and transmits the breath analysis test message via the wireless telephony network.

15 Claims, 3 Drawing Sheets

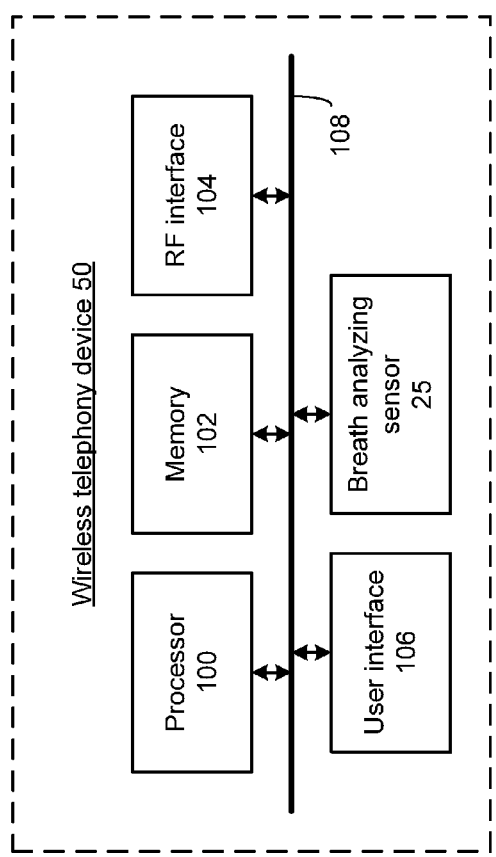
FIG. 2
FIG. 4
FIG. 3

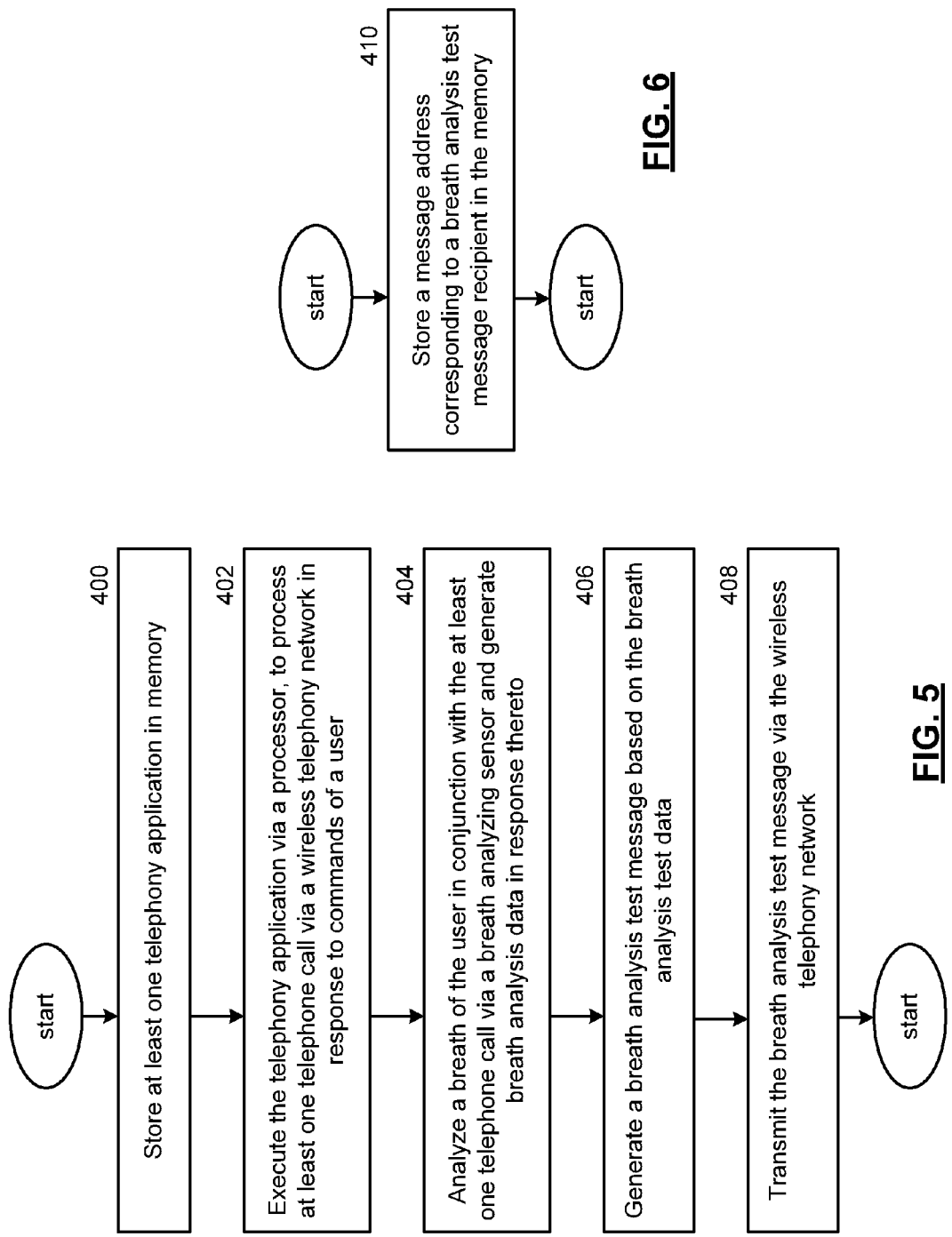

WIRELESS TELEPHONY DEVICE WITH BREATH ANALYSIS SENSOR AND METHODS FOR USE THEREWITH

CROSS REFERENCE TO RELATED PATENTS

The present U.S. Utility patent application claims priority pursuant to 35 U.S.C. §120, as a continuation, to U.S. Utility patent application Ser. No. 12/403,513, entitled WIRELESS TELEPHONY DEVICE WITH BREATH ANALYSIS SENSOR AND METHODS FOR USE THEREWITH, filed Mar. 13, 2009, which is hereby incorporated herein by reference in its entirety and made part of the present U.S. Utility patent application for all purposes:

BACKGROUND OF THE INVENTION

1. Technical Field of the Invention

The present invention relates to wireless communication devices used for placing telephone calls over a wireless telephony network.

2. Description of Related Art

Wireless telephones are commonly used to place telephone calls over wireless telephone networks. Examples of such networks include wireless telephone networks that operate via services such as cellular, personal communications service (PCS), general packet radio service (GPRS), global system for mobile communications (GSM), and integrated digital enhanced network (iDEN). These networks are capable of accessing the plain old telephone service (POTS) network as well as broadband data networks that provide Internet access and enhanced services such as streaming audio and video, television service, etc., in accordance with international wireless communications standards such as 2G, 2.5G and 3G.

Handheld breath analyzing devices, commonly known as "breathalyzers", are used to estimate the amount of alcohol in a person's blood. In many states, law enforcement personnel employ these devices to perform on-site sobriety tests of drivers suspected of being intoxicated. U.S. Pat. No. 7,341,693 to Der Ghazarian presents a radio frequency (RF) breathalyzer system, which transmits a unique RF signal in response to a toxic or non-toxic breath sample given to a RF breathalyzer by the user. An immobilizer CPU is installed in a vehicle to receive commands from the RF breathalyzer and to control a horn and lights of a vehicle, to immobilize the engine, and is connected to a GPS antenna driver through a mobile phone/pager unit to communicate with a monitoring station.

The disadvantages of traditional approaches will be apparent to one skilled in the art when presented the disclosure of the present invention as reflected in the enclosed drawings, claims and accompanying description.

BRIEF DESCRIPTION OF THE SEVERAL VIEWS OF THE DRAWINGS

FIG. 2 presents a block diagram representation of wireless telephony device 50 in accordance with an embodiment of the present invention.

FIG. 3 presents a pictorial representation of a breath analysis test message in accordance with an embodiment of the present invention.

FIG. 4 presents a pictorial representation of a breath analysis test message in accordance with another embodiment of the present invention.

FIGS. 5-6 present flowchart representations of methods in accordance with embodiments of the present invention.

DETAILED DESCRIPTION OF THE INVENTION

Figure 1:
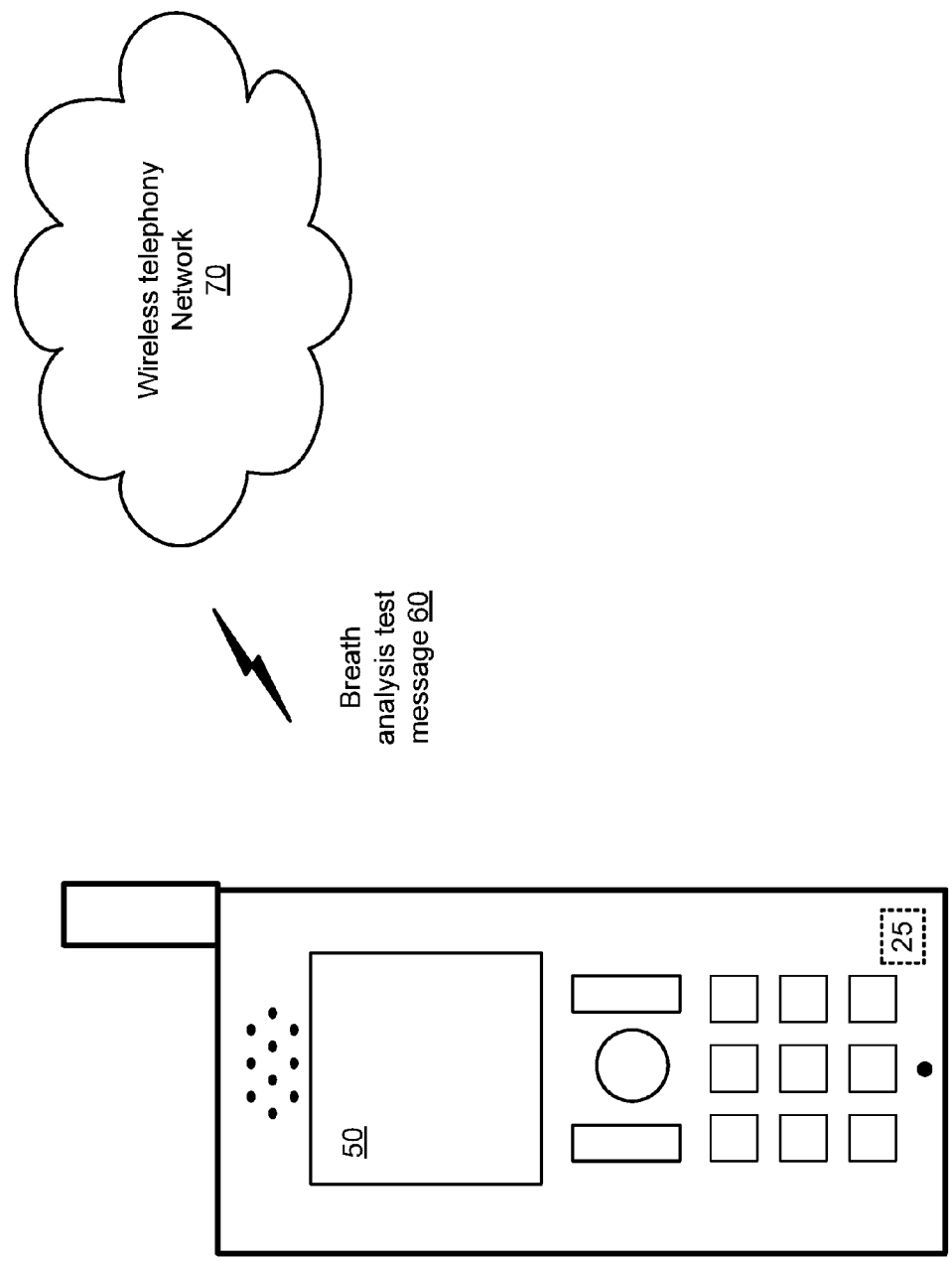
FIG. 1 presents a pictorial representation of a wireless telephony device 50 in accordance with an embodiment of the present invention.

FIG. 1 presents a pictorial representation of a wireless telephony device 50 in accordance with an embodiment of the present invention. In particular, a wireless wireless telephony device 50 communicates over a wireless telephony network 70 that is operably coupled to a plan old telephone service (POTS) network and data network such as the Internet. In an embodiment of the present invention, wireless telephony network 70 includes a wireless telephone network such as a cellular, PCS, GPRS, GSM, iDEN or other wireless communications network capable of sending and receiving telephone calls text messages, such as short message service (SMS) messages, email or other data messages that may include multimedia elements such as documents, audio files, video files, images and other graphics.

In an embodiment of the present invention, the wireless telephony device 50 includes a breath analyzing sensor 25. When a user places a telephone call or receives a telephone call via the wireless telephone device 50, the breath analyzing sensor 25 analyzes the breath of the user as the user speaks into the wireless telephony device 50 in conjunction with the telephone call. In response, the breath analyzing sensor 25 generates breath analysis test data. The wireless telephone device 50 generates a breath analysis test message 60, such as an email or text message, based on the breath analysis test data and transmits the breath analysis test message 60 via the wireless telephony network 70.

The operation of wireless telephony device 50 can be described in conjunction with the following example. In this embodiment, the wireless telephony device 50 is a cellular phone provided by a parent for use by a teenage son or daughter. An email or text messaging address of the parent is stored in a memory of the phone during set-up of the wireless telephony device 50. When the teenager uses the phone, his or her breath is analyzed for alcohol content. A text message is sent to the parent, either for each call made or received only in circumstances when the estimated blood alcohol content is above a threshold that is either selected by the parent during the set-up of the wireless telephony device 50 or is pre-stored.

For instance, the parent requires the son or daughter to call home before leaving a party on a Saturday night. When the teenager is about to leave they call home using the wireless telephony device 50. If the teenager has been engaged in drinking, the breath analyzing sensor 25 generates breath analysis test data that indicates an unacceptable blood alcohol level. The results of this test are sent to the parent via a text message, either during the call or shortly thereafter. In response the parent tells the teenager during the call or calls the teenager back to inform the teenager that the teenager is not allowed to drive and that the parent will come and pick up the teenager and bring him or her home.

FIG. 2 presents a block diagram representation of wireless telephony device 50 in accordance with an embodiment of the present invention. In particular, wireless telephony device 50 includes a processor 100 and memory module 102, an RF interface 104, a user interface 106 and breath analyzing sensor 25 that communicate via bus 108. These modules may be implemented using hardware, firmware, software or a combination thereof, in accordance with the broad scope of the present invention. While a particular bus architecture is shown in FIG. 2, alternative bus architectures that include further connectivity, such as direct connectivity between the various modules, are likewise possible to implement the features and functions included in the various embodiments of the present invention.

In an embodiment of the present invention, memory 102 stores operational instructions such as system programs, application programs, and other routines including a wireless telephony application and an corresponding set-up routine that are executed by the processor 100 to implement the various functions and features of the wireless telephony device 50. In particular, the telephony application provides functionally to send and receive telephone calls, text messages and email and to optionally browse the World Wide Web under commands of the user. In addition, the telephony application can generate and transmit automatically generated email and/or text messages in the form of breath analysis test message 60.

The processor of processor 100 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 102. Note that when the processor 100 implements one or more of its functions via a state machine, analog circuitry, digital circuitry, and/or logic circuitry, the memory 102 storing the corresponding operational instructions may be embedded within, or external to, the circuitry comprising the state machine, analog circuitry, digital circuitry, and/or logic circuitry. The memory 102 may be a single memory device or a plurality of memory devices. Such a memory device may be a read-only memory, random access memory, volatile memory, non-volatile memory, static memory, dynamic memory, flash memory, cache memory, removable memory card and/or any device that stores digital information.

Wireless telephony device 50 further includes an RF interface such as an RF transceiver for wireless communication with wireless telephony network 70. User interface 106 responds to commands from the user and otherwise provides a user interface, such as a graphical user interface. User interface 106 includes an audio input device such as microphone and an audio output device such as speaker, a display screen such as a touch screen or non-touch sensitive display, a keypad, a pointing device, a headphone jack, and/or a camera, along with a plurality of drivers for interfacing these display devices to the processor 100.

Breath analyzing sensor 25 can include a spectrophotometer such as an infrared spectrophotometer, electrochemical fuel cell or other gas analyzer that analyzes the breath of the user of wireless telephony device 50 to detect the presence and concentration of alcohols, such as ethanol and methanol, acetone or other hydrocarbons that indicate the blood alcohol level of the user. In an embodiment of the present invention, the breath analyzing sensor 25 is coupled to an orifice in the housing of wireless telephony device 50 used by the microphone included in user interface 106. In another embodiment, the breath analyzing sensor 25 is coupled to an orifice in the housing of wireless telephony device 50 that is in proximity to an orifice used by the microphone included in user interface 106. In either case, the breath analyzing sensor 25 is configured to analyze the breath of the user when the user is talking into the microphone during ordinary use in conjunction with a telephone call. While the breath analyzing sensor 25 is described above as being implemented in a permanent position within the wireless telephony device 50, in an embodiment of the present invention, the breath analyzing sensor 25 can be removableably connected to the wireless telephony device 50, via a port within the battery compartment or via an external port. Further the breath analyzing sensor 25 can be incorporated in a SIM card or battery used in conjunction with the wireless telephony device 50.

As discussed in conjunction with FIG. 1, an email or text messaging address of the breath analysis test message 60 is stored in memory 102 during set-up of the wireless telephony device 50. In addition, memory 102 stores a test threshold, such as 0.01%, 0.02%, 0.04%, 0.08% or some other blood alcohol level, that is either selected by the parent during the set-up of the wireless telephony device 50 or is pre-stored in the memory 102. This test threshold can be used to generate breath analysis test results, such as an indication of whether or not a particular blood alcohol level of the user passes or fails. In particular, the telephony application can compare the breath analysis test data the test threshold and generate breath analysis test results in response thereto. In this fashion, the breath analysis test message 60 can include the breath analysis test results.

In another embodiment of the present invention, the breath analysis test results can be used by the telephony application to trigger the transmission of a breath analysis test message 60. For instance, the breath analyzing sensor 25 can analyze the breath of the user during each call sent or received via the wireless telephony device 50. If the breath analysis test results indicate that the blood alcohol level of the user is above the test threshold, the breath analysis test message 60 is transmitted. However, if the breath analysis test results indicate that the blood alcohol level of the user is below the test threshold, no breath analysis test message 60 is transmitted. The conditions for sending a breath analysis test message 60, such as for every call, or only for calls where the breath analysis test results indicate that the blood alcohol level of the user is above the test threshold, can also be established during the set-up of the wireless telephony device 50.

While the wireless telephony device 50 has been described above in conjunction with a parent/child relationship, other scenarios are likewise possible including the use of the wireless telephony device 50 for employee monitoring, parolee monitoring, home incarceration, minimum supervisory reporting, insurance compliance programs or other scenarios where it is desirable to monitor the alcohol use by the user of the wireless telephony device 50. Further, in one or more of these scenarios, the test threshold may be set such that any measurable alcohol use by the user could trigger a failed test.

FIG. 3 presents a pictorial representation of a breath analysis test message in accordance with an embodiment of the present invention. In particular, a breath analysis test message 110 is shown that is generated and transmitted by wireless telephony device 50. As shown, the breath analysis test message 110 includes an identification of the particular wireless telephony device 50 by its telephone number, however, in other embodiments, additional or other text that indicates the name of the user of the phone or other phone identification, e.g. "Bobby's Phone", can likewise be employed. As further shown, the breath analysis test message 110 also includes breath analysis test results indicating that the user's blood alcohol level failed the test by being at or above the test threshold. Further the specific breath analysis test data indicating a blood alcohol level of 0.09% is further included.

FIG. 4 presents a pictorial representation of a breath analysis test message in accordance with another embodiment of the present invention. In particular, a breath analysis test message 120 is shown that is generated and transmitted by wireless telephony device 50 in an embodiment where such messages are sent for every call. As shown, the breath analysis test message 120 includes breath analysis test results indicating that the user's blood alcohol level passed the test by being below the test threshold. Further the specific breath analysis test data indicating a blood alcohol level of 0.01% is further included.

FIG. 5 presents a flowchart representation of a method in accordance with an embodiment of the present invention. In particular, a method is presented for use in conjunction with one or more of the functions and features described in conjunction with FIGS. 1-4. In step 400, at least one telephony application is stored in a memory. In step 402, the telephony application is executed via a processor, to process at least one telephone call via a wireless telephony network in response to commands of a user. In step 404, the breath of the user obtained in conjunction with the at least one telephone call is analyzed via a breath analyzing sensor and breath analysis test data is generated in response thereto. In step 406, a breath analysis test message is generated based on the breath analysis test data. In step 408, the breath analysis test message is transmitted via the wireless telephony network.

In an embodiment of the present invention, step 404 includes analyzing the breath of the user when the user speaks into the wireless telephony device during the at least one telephone call. Step 406 can include: comparing the breath analysis test data to at least one test threshold; and generating breath analysis test results in response thereto, wherein the breath analysis test message includes the breath analysis test results. The breath analysis test message can be a text message or an email message.

FIG. 6 presents a flowchart representation of a method in accordance with an embodiment of the present invention. In particular, a method is presented for use in conjunction with one or more of the functions and features described in conjunction with FIGS. 1-5. In step 410, a message address, corresponding to a breath analysis test message recipient, is stored in the memory and step 408 includes transmitting the breath analysis test message to the message address.

Thus, there has been described herein an apparatus and method, as well as several embodiments including a preferred embodiment, for implementing a wireless telephony device. Various embodiments of the present invention herein-described have features that distinguish the present invention from the prior art.

It will be apparent to those skilled in the art that the disclosed invention may be modified in numerous ways and may assume many embodiments other than the preferred forms specifically set out and described above. Accordingly, it is intended by the appended claims to cover all modifications of the invention which fall within the true spirit and scope of the invention.

What is claimed is:

1. A wireless telephony device comprising:
a memory that stores at least one telephony application, a messaging address and a test threshold;
a processor, coupled to the memory, that executes the telephony application to process at least one telephone call via a wireless telephony network in response to commands of a user; and
a breath analyzing sensor, coupled to the processor, that analyzes a breath of the user in conjunction with the at least one telephone call generates breath analysis test data in response thereto, and compares the breath analysis test data to the test threshold, wherein the breath analyzing sensor is incorporated into at least one of: a SIM card of the wireless telephony device, and a battery of the wireless telephony device;
wherein, when the breath analysis test data exceeds the test threshold, the telephony application automatically generates a breath analysis test message, based on the breath analysis test data and transmits the breath analysis test message to the third party at the messaging address via the wireless telephony network.

2. The wireless telephony device of claim 1 wherein the breath analyzing sensor analyzes the breath of the user when the user speaks into the wireless telephony device during the at least one telephone call.

3. The wireless telephony device of claim 1 wherein the breath analyzing sensor is removably connected to the wireless telephony device via a port within a battery compartment of the wireless telephony device.

4. The wireless telephony device of claim 1 further comprising:
a user interface, coupled to the memory, for receiving the messaging address from a third party.

5. The wireless telephony device of claim 1 further comprising:
a user interface, coupled to the memory, for receiving selection of the test threshold from a third party.

6. The wireless telephony device of claim 1 wherein the breath analysis test message is one of: a text message, and an email message.

7. A method for use in a wireless telephony device, the method comprising:
storing a messaging address, a test threshold and at least one telephony application in a memory;
executing the telephony application via a processor, to process at least one telephone call via a wireless telephony network in response to commands of a user; and
analyzing a breath of the user and generating breath analysis test data in response thereto wherein the breath analyzing sensor is incorporated into at least one of: a SIM card of the wireless telephony device, and a battery of the wireless telephony device;
comparing the breath analysis test data to the test threshold;
automatically generating a breath analysis test message based on the breath analysis test data when the breath analysis test data exceeds the test threshold; and
transmitting the breath analysis test message via the wireless telephony network.

8. The method of claim 7 wherein analyzing breath of the user includes analyzing the breath of the user when the user speaks into the wireless telephony device during the at least one telephone call.

9. The method of claim 7 wherein the breath analysis test message includes the breath analysis test data.

10. The method of claim 7 wherein transmitting the breath analysis test message includes transmitting the breath analysis test message to the messaging address associated with a third party.

11. The method of claim 7 wherein the breath analysis test message is a text message.

12. The method of claim 7 wherein the breath analysis test message is an email message.

13. The method of claim 7 further comprising:
receiving, via a user interface, the messaging address from a third party.

14. The method of claim 7 further comprising:
receiving, via a user interface, selection of the test threshold from a third party.

15. A wireless telephony device comprising:
   a memory that stores at least one telephony application, a messaging address and a test threshold;
   a processor, coupled to the memory, that executes the telephony application to process at least one telephone call via a wireless telephony network in response to commands of a user; and
   a breath analyzing sensor, coupled to the processor, and removable connected to the wireless telephony device via a port within a battery compartment of the wireless telephony device, that analyzes a breath of the user and generates breath analysis test data in response thereto, wherein the breath analyzing sensor is incorporated into at least one of: a SIM card of the wireless telephony device, and a battery of the wireless telephony device;
   wherein, when the breath analysis test data exceeds the test threshold, the telephony application automatically generates a breath analysis test message, based on the breath analysis test data and transmits the breath analysis test message as a text message via the wireless telephony network.

* * * * *